(12) United States Patent
Menozzi et al.

(10) Patent No.: US 6,350,032 B1
(45) Date of Patent: Feb. 26, 2002

(54) VISION TESTING APPARATUS

(75) Inventors: Marino Menozzi, Bonstetten; Christoph Zeller, Winterthur, both of (CH)

(73) Assignee: Titmus Optical, Inc., Petersburg, VA (US)

( * ) Notice: Subject to any disclaimer, the term of this patent is extended or adjusted under 35 U.S.C. 154(b) by 0 days.

(21) Appl. No.: 09/500,922

(22) Filed: Feb. 9, 2000

(51) Int. Cl.[7] .................................................. A61B 3/02
(52) U.S. Cl. ...................................................... 351/239
(58) Field of Search ................................. 351/205, 211, 351/221, 239, 243, 244, 245, 246, 233

(56) References Cited

U.S. PATENT DOCUMENTS

| | | |
|---|---|---|
| 3,936,163 A | 2/1976 | Toth |
| 4,192,582 A | 3/1980 | Aoki et al. |
| 4,740,072 A * | 4/1988 | Griffen et al. ............... 351/243 |
| 5,483,305 A | 1/1996 | Kohayakawa |
| 5,617,157 A | 4/1997 | Shalon et al. |
| 5,825,460 A | 10/1998 | Kohayakawa |
| 6,149,275 A * | 11/2000 | O'Shea ....................... 351/233 |

FOREIGN PATENT DOCUMENTS

| | | |
|---|---|---|
| EP | 0045897 | 2/1982 |
| EP | 0487073 | 11/1991 |
| GB | 2059623 | 4/1981 |

* cited by examiner

Primary Examiner—George Manuel
(74) Attorney, Agent, or Firm—Millen, White, Zelano & Branigan, P.C.

(57) ABSTRACT

A vision test apparatus includes a light occluding casing and viewer connected to the casing which comprises a front lens. A mirror is rotatably mounted to the inside of the casing behind the front lens. An image display is movably mounted to the inside of the casing. An auxiliary lens is movably mounted to the inside of the casing and in alignment between the image display and the mirror whereby an image that is displayed on the image display passes through the auxiliary lens reflects off of the mirror and passes through the front lens.

19 Claims, 8 Drawing Sheets

VISION TESTING APPARATUS

BACKGROUND OF THE INVENTION

The present invention relates to the field of ophthalmic instruments, and more particularly, to an improved vision tester designed for accurate and precise measurement of visual performance over a variable range of testing distances. The present invention is designed to provide a variety of standard and/or customized vision tests in a relatively small, compact, lightweight, and portable instrument.

Conventional vision testers are described in U.S. Pat. No. 4,740,072. Examples of prior art vision testers are discussed in that patent. That discussion is incorporated by reference herein.

Since the issuance of the '072 patent, additional vision testers have been suggested including a self testing device described in PCT Application No. PCT/IL97/00220 (International Publication No. WO 98/02083). This application describes a computer-controlled self testing device such as a vision screener. Unfortunately, this computer-controlled device still incorporates many of the drawbacks of conventional testers including testing over a limited number of vision testing distances.

Despite the evolution of vision testing technology generally, there remain drawbacks in existing vision testers. First, there exist apparatuses with tests for near and far vision. Further, as described in the '072 patent, there may also be intermediate distance tests that may be administered depending on the manual insertion of different lenses and/or prisms in the apparatus. These arbitrary lenses can be inserted in the screener to reproduce different visual distances seen by a test subject. Unfortunately, this testing is very arbitrary, because it can only test certain distances. There is limited variability in the test equipment based solely on the various lenses and prisms that may be inserted into the apparatus.

Second, vision testers that use bulbs or other light sources shining through, for instance, a slide, do not allow for variability in the size of the image presented. In other words, the image itself cannot be enlarged or reduced. The only way to accomplish this variability is to have a plurality of different slides, with each slide having different-sized images. This means an arbitrary library of images that an administrator is limited to.

Also, in some devices, testing vision at different distances requires a different orientation of gaze. Test subjects must be made aware of this fact, and some subjects who do not have experience in the use of multifocal lenses (tilting the head for gazing at different distances) might have problems in realizing this requirement.

SUMMARY OF THE INVENTION

Accordingly, it is an object of the present invention to overcome the foregoing drawbacks and provide a vision testing apparatus that solves those problems.

Specifically, the present invention includes a vision test apparatus comprising a light occluding casing. A viewer is connected to the casing and comprises a front lens. A mirror is rotatably mounted to the inside of the casing and behind the front lens. An image display is movably mounted to the inside of the casing. And an auxiliary lens is movably mounted to the inside of the casing and in alignment between the image display and the mirror whereby an image that is displayed on the image display passes through the auxiliary lens, reflects off the mirror and passes through the front lens.

In another embodiment, the invention includes a vision test apparatus comprising a light occluding casing. A viewer is connected to the casing and comprises right and left front lenses. A right mirror and a left mirror are each rotatably mounted to the inside of the casing behind the corresponding right and left front lenses. A right image display and a left image display are movably mounted to the inside of the casing wherein the image displays face each other with each display being generally perpendicular to a line between the corresponding front lenses and mirrors.

In a further embodiment, the vision test apparatus comprises a light occluding casing. Viewing means are fixably attached to the casing. Mirror means are rotatably mounted behind the viewing means for reflecting images from an image display means to the viewing means. There is also included a means for generating images, and an auxiliary lens movably mounted to the casing between the image displays means and the mirror means.

DETAILED DESCRIPTION OF A PREFERRED EMBODIMENT

Figure 1:
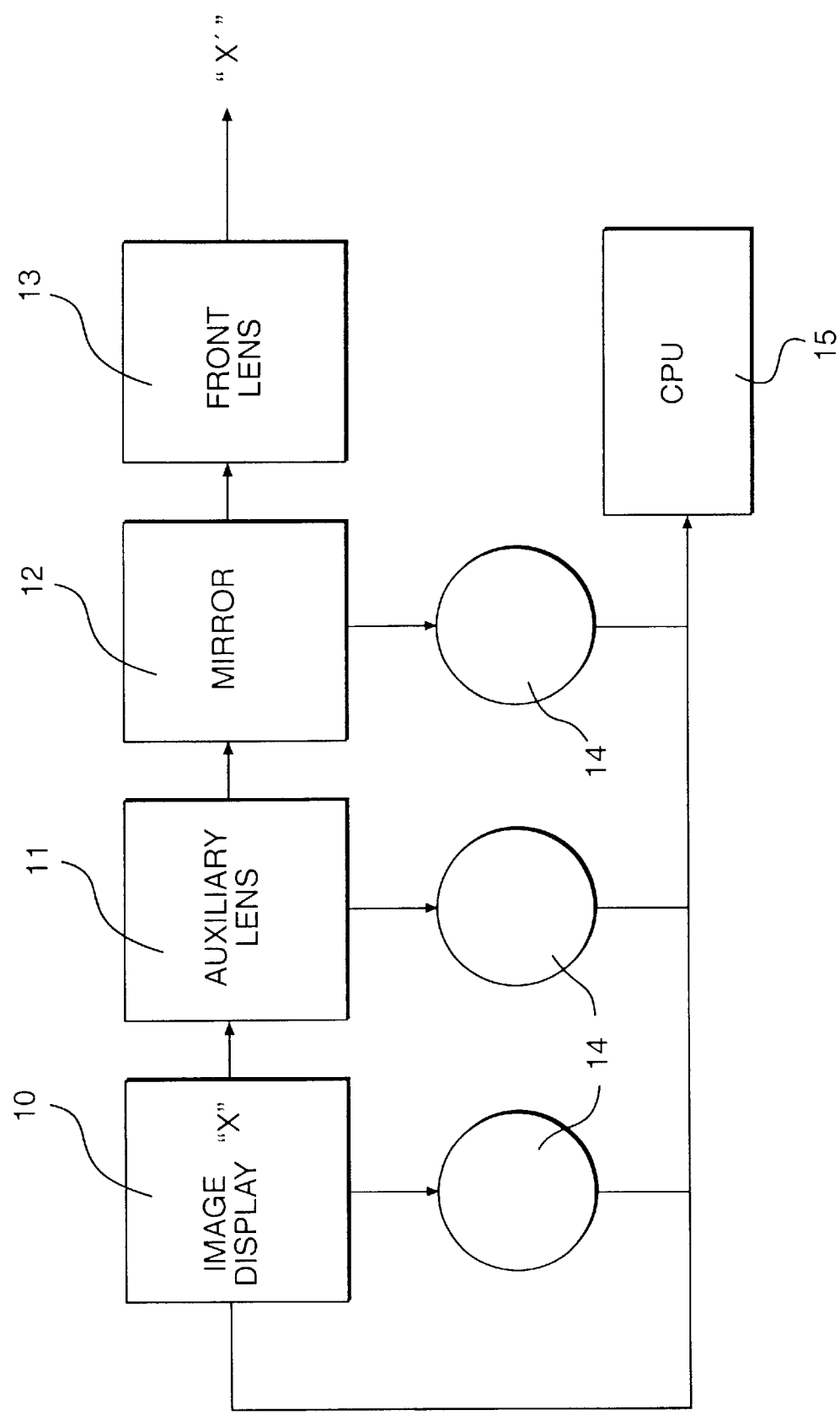
FIG. 1 is a schematic flow chart illustrating components of a preferred embodiment of the present vision tester invention.

The invention will be described in the context of a preferred embodiment. FIG. 1 demonstrates a simple schematic of a vision screener where an image "x" is presented on an image display 10. The image "x" then passes through an auxiliary lens 11, is reflected off of a mirror 12, and finally passes through a front lens 13. As a result of passing through the lenses 11 and 13, the image "x" may appear differently to a test subject as virtual image "x". Motors 14 are controlled by a CPU 15 that controls the positioning of the image display 10, auxiliary lens 11 and mirror 12. The CPU 15 also controls the image "x" presented on the image display 10. In this preferred embodiment, the vision screener displays different optotypes (and other pictures for vision testing) at distances between 355 mm and 6 m (14 inches and 20 feet) with an optional prism of ±5cm/m (prism diopters).

In order to perform certain vision tests requiring stereoscopic images, independent images for the left and right eye are required. A preferred vision screener, therefore, uses a separate image display 10 for each eye. Both the auxiliary lens 11 and the image display 10 are movable independently of each other along a common axis, offering the possibility to not only physically move the image position in relation to the front lens 13 but to vary the image size as well. The mirrors 12 are used to compensate for the vergence of the eyes of a test subject and to give an additional range used for lateral prisms in the range of ±5 cm/m. The mirrors 12 are turned and moved in a coupled way so that the optical path always remains aligned with the optical path of the auxiliary lenses and screens effectively reducing effects due to spherical "aberration" of the auxiliary lenses 11.

Figure 2:
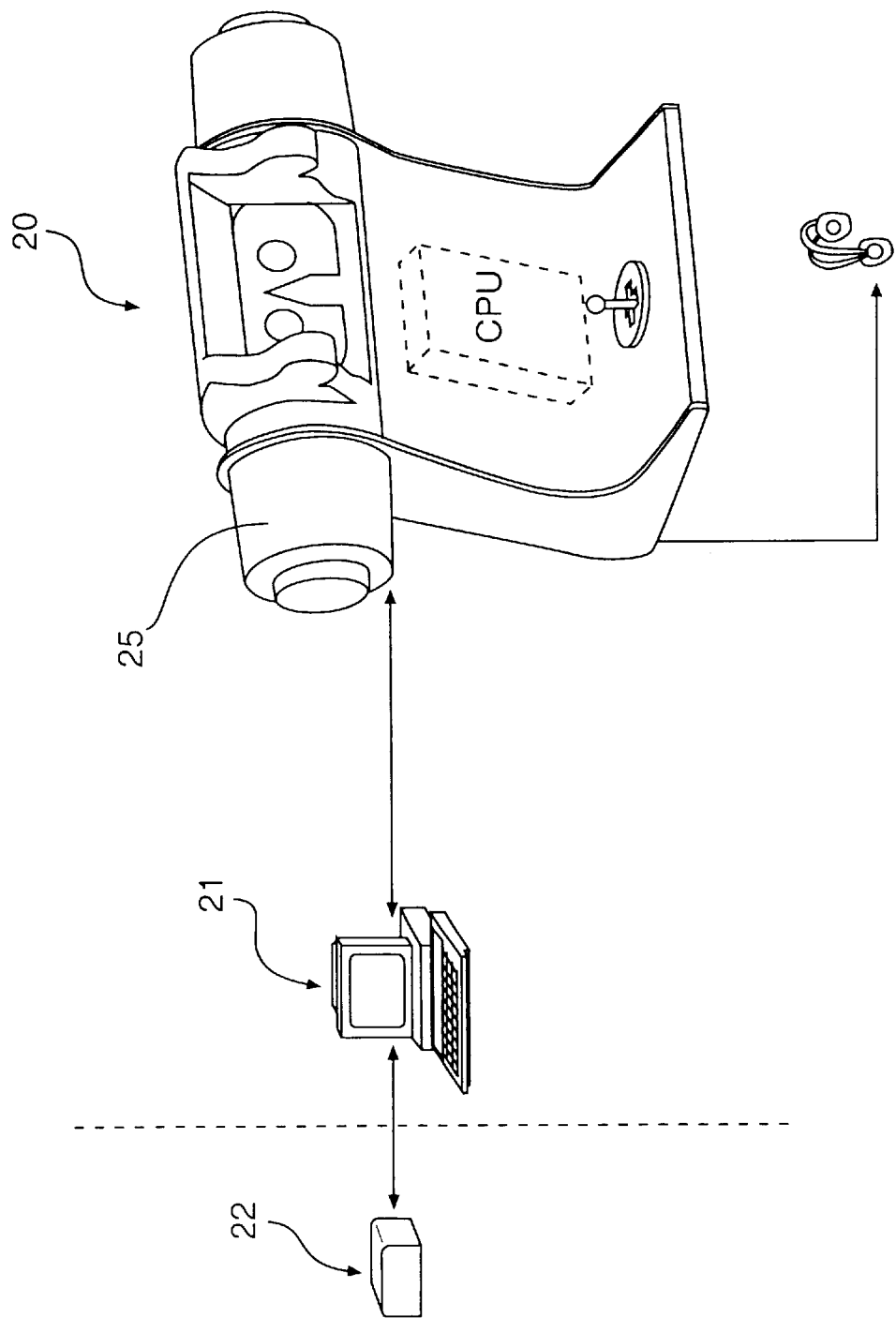
FIG. 2 is perspective schematic view of a vision tester in accordance with the present invention connected to a PC and a local area network.

FIG. 2 illustrates how the preferred embodiment of a vision screener 20 is electronically connected to an administrating computer 21 which may further be connected to a local area network 22. In this way, test results may be compiled, stored and recalled as necessary. Also, custom tests can be created and administered as desired.

Image Requirements

If testing visual acuity, the typical distances for this test are given by international standards which are set forth in the following table:

TABLE 1

| | Distance Near | Far |
|---|---|---|
| USA | 14"(355 mm) | 20'(6 m) |
| Europe | 400 mm | 5 m |

Figure 3:
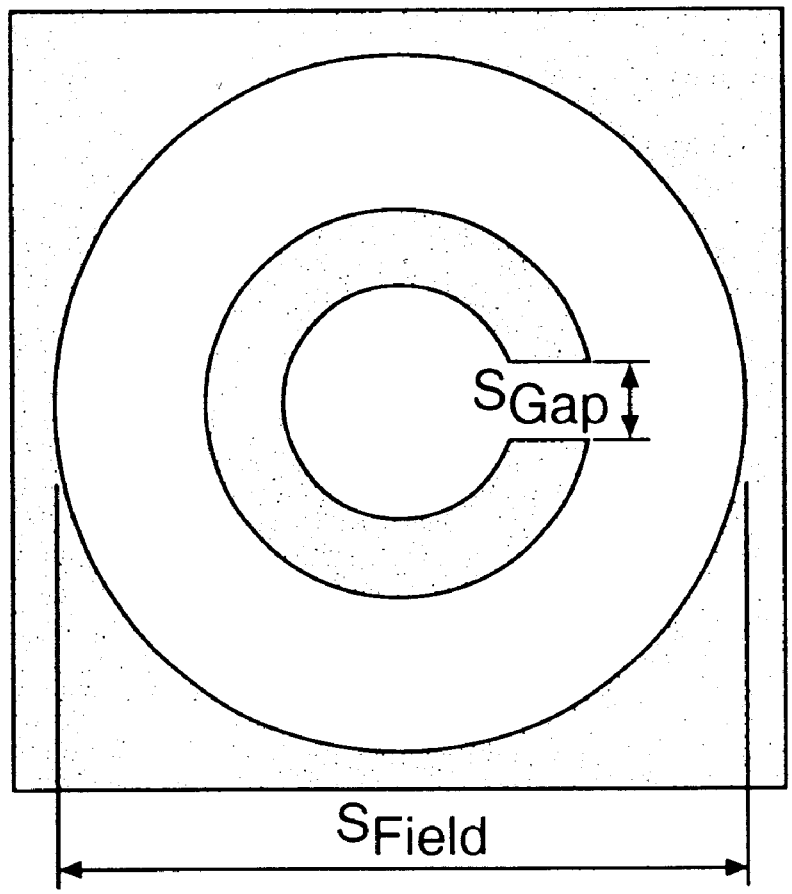
FIG. 3 is a representative Landolt Ring image that is used in connection with a preferred embodiment of the present invention.

A Landolt Ring, as shown in FIG. 3, is a conventional image that is used for far and near testing. In the example of a Landolt Ring test, a visual acuity of 1.0("normal" vision) means that the gap Sgap in FIG. 3 should appear under an angle of one minute of arc. Smaller visual acuity values mean larger angles. The maximum value to test is usually 1.6 or 2.0. Higher values cannot be discriminated by most people.

Referring now to the example of the Landolt Ring in FIG. 3, the $S_{Gap}$ is the size of the gap of a Landolt Ring, and the $S_{Field}$ is the size of the white field the Landolt Ring is displayed on. The size of the field and the gap can be calculated using the following formulas:

$$S_{Gap} = dist \cdot \tan\frac{1°}{60}$$

$$S_{Field} = dist \tan(2°)$$

where "dist" refers to the distance between the nodal point of the eye and the image. Using the examples of the desired testing distances from Table 1, the image sizes for the different distances are as follows:

TABLE 2

Image Sizes for Different Distances

| Distance | $S_{Gap}$ | $S_{Field}$ |
|---|---|---|
| 355 mm | 51.63 μm | 12.40 mm |
| 6000 mm | 872.6 μm | 209.5 mm |

Acuity testing requires optotypes with varying demand of acuity to be presented in several viewing distances to the testee. Ranges of acuity usually vary between 0.1 and 1.25 (decimal acuity). Viewing distances may vary in a range between a near (e.g. 0.35 m) and a far (e.g. 6 m) distance. Monitors of computers hardly meet optical requirements for displaying optotypes under conditions mentioned above. It is much more convenient to combine a small high-resolution monitor with lenses so to build a variable optical system. The system has the advantage of being much less space consuming and cheaper.

Figure 4:
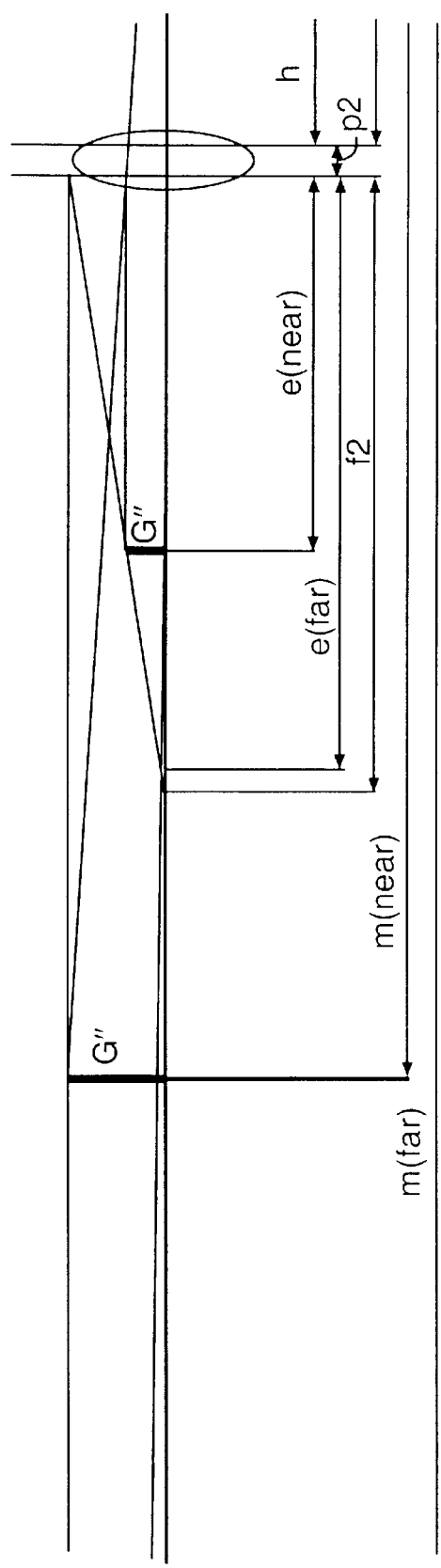
FIG. 4 is a schematic drawing defining symbols in a formula used to select the size of an object displayed on an image display in accordance with a preferred embodiment of the present invention.

If using a 200 mm front lens to project the image to a virtual image at the given distances for the near and far tests, the real image has to be shown at distances calculated using the following formulas and also with reference to FIG. 4:

| m(near) | distance between nodal point and virtual image for near distance |
| m(far) | distance between nodal point and virtual image for far distance |
| f2 | focal length of the collimator lens |
| p2 | thickness of the collimator lens |
| h | distance between H1 and front of eye |
| e(near) | distance between H2 and the object for near distance |
| e(far) | distance between H2 and the object for far distance |
| G" | size of virtual image |
| G' | since of object |
| H1 | principle plane of lens |
| H2 | principle plane of lens |

$$e = \frac{1}{\frac{1}{f_2} + \frac{1}{(m - h - k_p)}}$$

$$G' = G'' \cdot \frac{f_2}{f_2 + (m - h - k_p)}$$

$$s' = s'' \cdot \frac{f_2}{f_2 + (m - h - k_p)}$$

TABLE 3

Projected Image

| Distance | e | Min. Gap Size | Field Size | Distance from Lens Middle point |
|---|---|---|---|---|
| 355 mm | 120.83 mm | 20.45 μm | 4.91 mm | 11.56 mm |
| 6 m | 193.5 mm | 28.38 μm | 6.80 mm | 0.95 mm |

As can be seen in Table 3, the sizes are much closer for the different tests as a result of the lens. Special care has to be taken that the images have to move apart from each other. This means that two independent images have to be used, but this has the advantage that it is possible to easily create stereoscopic displays without the need of special glasses. The screen used in this configuration needs a minimum resolution (dot pitch) of 10 μm and a minimum number of 665 pixels. This is about the amount of pixels a commercially available high-resolution display offers. Currently available image displays that meet these requirements include those manufactured by Display Tech and Colorado Micro Display.

Figure 5:
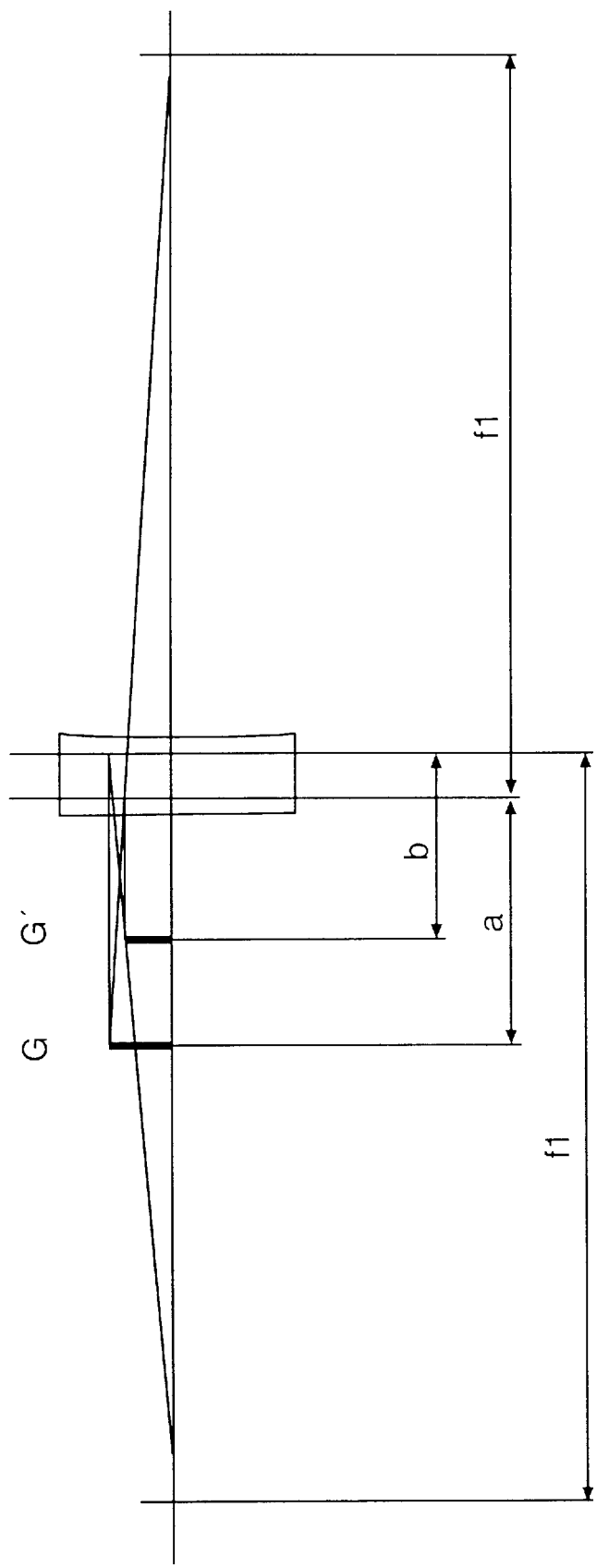
FIG. 5 is a schematic drawing defining symbols in a formula used to calculate the proper distance between an image and an auxiliary lens incorporated in an preferred embodiment of the present invention.

Another problem in using an image display screen is that the required size of the pixels is about 10 μm and a minimum number of 665 pixels. Unfortunately, the smallest dot pitch currently available is 12 to 13 μm. The screen on the image display therefore has to be optically reduced in size. By using a negative auxiliary lens, the pixel sizes may be varied by altering the distance between the screen and the auxiliary lens. Variable pixel sizes have the advantage that interpolation errors due to different image sizes can theoretically be avoided. With reference to FIG. 5, the formulas to calculate the distances between an image and an auxiliary lens are:

| | | |
|---|---|---|
| | fl | focal length |
| | G | size of object |
| | G' | size of virtual image |
| | a | distance between H1 and object |
| | b | distance between H2 and object |

$$a = f_1 \cdot \left(1 - \frac{G}{G'}\right)$$

$$b = f_1 \cdot \left(\frac{G'}{G} - 1\right)$$

By using these formulas, the distance between the auxiliary lens and the image display can be calculated depending on the testing sought to be performed.

The Mirrors

Since our "preferred" vision screener is intended to be used for testing of stereoscopic vision, the screens must enable the simultaneous presentation of two separate images. A way to achieve this is to present the two images on two physically separated displays. The separation of the displays depends on the optical setup. Because the distance between the displays is small, the right and left displays have to be separated in a way that allows the vision screener to test intermediate distances as well. One solution, using prisms, leads to the problem that each display still has to be moved in two independent directions. An alternative would be to use different prisms for every distance used, but prisms are relatively expensive and the mechanics to always put the right prism in a vision screener is not trivial. Prisms that can change their value are also known under the name Herschel-prism, but those are quite expensive. Since the image displays and auxiliary lenses in the preferred embodiment of a vision screener use motors to move along an axis, a motor can be used to turn a mirror as well.

When trying to get the images to only one axis (to present a single image to a viewer), the mirrors should turn along a rotation point which is not accessible because it is too close to the eyes. To get the same effect, the mirrors have to be turned around a moving rotation point so that the mirror effectively moves and turns at the same time. This goal can be achieved using a wedge against which the turning mechanism is mounted. Required motion of the mirror to enable "natural" viewing conditions is complex. It requires mirrors to be moved on a two dimensional path. This would require the use of two separate motors. In order to avoid to use two motors in this task, a wedge or rail serves as a kind of a stop against which one edge of the mirror is pulled (by means of springs). The shape of the rail is such to allow the mirror to fulfill the required two dimensional travel when it is tracked by the belt, which again serves both mirrors.

Figure 6:
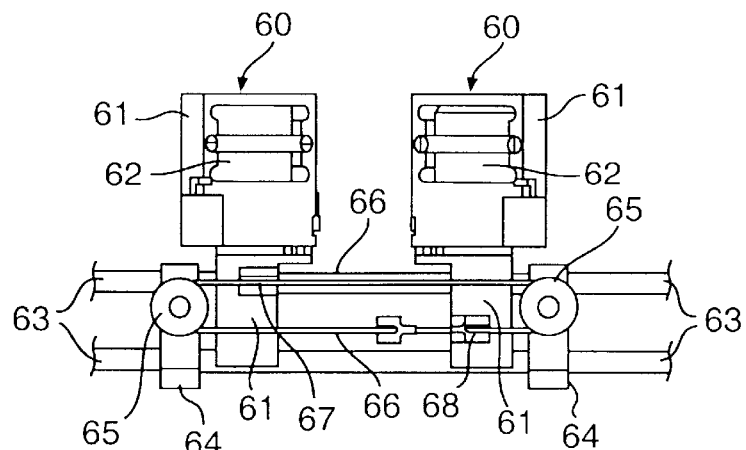
FIG. 6 is a front elevation view of the mirror-related components of a vision screener in accordance with a preferred embodiment of the present invention.
Figure 7:
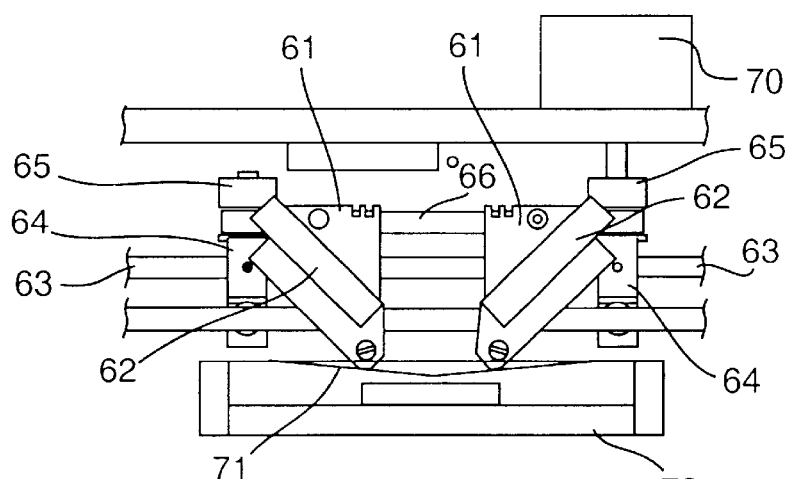
FIG. 7 is a top elevation view of the mirror-related components of a vision screener in accordance with a preferred embodiment of the present invention.

Referring now specifically to FIGS. 6 and 7, a mirror assembly 60 includes a frame component 61 and a mirror 62. Both FIGS. 6 and 7 illustrate two mirror components. One for the right eye and one for the left eye. They are referred to herein interchangeably. The frame component 61 is movably connected to support bars 63. The support bars 63, are anchored to the platform that is mounted inside a vision screener. The mounts 64 are fixedly connected to the support bars 63. Also, cogwheels 65 are rotatably mounted on the mounts 64. The cogwheels 65 are connected by a belt 66. The top of the belt 66 is connected to one of the supports 61 at anchor point 67. The other support 61 is connected to the belt 66 at anchor point 68. By connecting the movable frame 61 to the respective top 67 and bottom 68, the turning of the cogwheel 65 will move the mirrors toward each other or away from each other depending on the rotation of the wheels 65.

In order to accomplish the moving rotation point discussed earlier, a wedge 71 is a specially machined surface against which the frame 61 of the mirror assembly 60 moves. The wedge 71 is preferably made a portion of the viewer 72. The specific angle of the wedge 71 will vary depending on the specific construction of a given vision tester having different distances from an image display to a mirror. In a preferred embodiment, the relative angle position dependency for the mirrors for far distance (6 m) testing using a 5 diopter front lens include the following points on a straight line: 20 mm—41.5°; and 32 mm—45°.

Selecting the Front Lens

The selection of the front lens is limited by several conditions. Given the fact that for the far distance test, a maximum error of 3% is typically allowed, and for the near distance test, a maximum error of 5% is typically allowed, the projected distances (e) for some lenses are as follows:

TABLE 4

| | | Tolerances for e | | |
|---|---|---|---|---|
| | Distance | Toler- | e in mm | |
| Lens | in mm | ance | min. | max |
| 150 mm | 6000 | 3% | 146.31 | 146.20 | 146.42 |
| | 355 | 5% | 100.55 | 99.36 | 101.68 |
| 180 mm | 6000 | 3% | 174.71 | 174.55 | 174.87 |
| | 355 | 5% | 113.20 | 111.70 | 115.55 |
| 200 mm | 6000 | 3% | 193.50 | 193.30 | 193.68 |
| | 355 | 5% | 120.79 | 119.09 | 123.48 |
| 250 mm | 6000 | 3% | 239.92 | 239.62 | 240.20 |
| | 355 | 5% | 137.39 | 133.67 | 140.88 |
| 300 mm | 6000 | 3% | 285.60 | 285.17 | 286.00 |
| | 355 | 5% | 151.24 | 146.74 | 155.48 |

Other limitations must also be factored into the front lens selection, the distance between the auxiliary lens and the screen is limited by the illumination of the screen which, in a preferred embodiment, uses a 45° beam splitter. The minimum distance between the screen and the auxiliary lens is therefore limited to about 30 mm. The distance of the virtual image to the auxiliary lens is then about 25 mm using a—100 mm auxiliary lens. In order to reduce the pixel size of the image formed by the auxiliary lens, the distance of the display must be increased by another 25 mm. The closest distance between the auxiliary lens and the mirror is achieved, when the optics is set up for near vision testing. Due to the fact that the mirror is tilted with respect to the optical axis (by about 45 degrees), the closest distance between mirror and auxiliary lens is limited to about 30 mm. For a similar reason, the closest distance between the mirror and the front lens is limited to about 40 mm. Assuming thickness of the auxiliary lens to be about 10 mm, we then can compute the total distance between the front lens and the image of the display. The total distance is 25 mm+30 mm+40 mm+10 mm=130 mm.

Selecting the Auxiliary Lens

The auxiliary lens is used to decrease the image size. In a preferred embodiment, the pixel size of the screen is 12 μm to 13 μm. If assuming a pixel size of 12 μm and the usage of 6 pixels with 10% (6×12 μm=72 μm) for a far distance of 1° (57 μm) one gets a minimum focal length, when assuming a minimum distance of 25 mm between the screen and the auxiliary lens, of $$f_{1min} = \frac{a_{min}}{1 - \frac{72 \text{ μm}}{56.76 \text{ μm}}} = \frac{25 \text{ mm}}{1 - 1.2685} = -93 \text{ mm}$$

For near distances, a smaller image is required leading to approximation problems when increasing visus. Mainly, decreasing the virtual images size is not practically possible because this would separate the auxiliary lens farther from the screen, which is impossible because of a lack of space. Therefore, the number of pixels used to display 1° must be reduced from 6 to 5 according to the difference in required image sizes. This also means that reducing or adding a pixel results in a 20% change of the gap size. The pixel size therefore needs to be adjusted so that this error can be reduced to an affordable level. Fortunately, a modification in size of 5% will be enough to achieve this requirement since the step in visus is 26%, and with increasing gap size, one gets the advantage that a pixel error becomes less important, so that one can change a whole pixel if necessary.

The gap size then calculates to 105% 12 μm=63 μm and the upper limit for the negative lens is thus:

$$f_{1max} = \frac{b_{max}}{\frac{40.9 \text{ μm}}{63 \text{ μm}} - 1} = \frac{35 \text{ mm}}{0.717 - 1} = -99.8 \text{ mm}$$

resulting in a negative lens of approximately −100 mm being preferable.

TABLE 5

Parameter Table for Different Auxiliary Lenses

| | b | | | a | | |
|---|---|---|---|---|---|---|
| Aux.Lens | norm (mm) | min (mm) | max (mm) | norm (mm) | min (mm) | max (mm) |
| −50 mm | 11.54 | 7.26 | 15.04 | 15.0 | 8.5 | 21.5 |
| −70 mm | 16.15 | 10.17 | 21.05 | 21.0 | 11.9 | 30.1 |
| −100 mm | 23.08 | 14.50 | 30.07 | 30.0 | 17.0 | 43.0 |
| −150 mm | 34.62 | 21.79 | 45.11 | 45.0 | 25.5 | 64.5 |
| −200 mm | 46.15 | 29.06 | 60.14 | 60.0 | 34.0 | 86.0 |

Overview of the Mechanics of a Preferred Embodiment

The image seen by a person being tested by the vision screener is generated by two independent screens, one for the left eye and one for the right eye. The image displays are moved in a plane perpendicular to the line of sight from the front lens to the mirror. In other words the right and left screens of the corresponding image displays are parallel to and face each other and move perpendicular to a line'from the front lens to the mirrors. Assuming that the mechanics are adjustable to 0.1 mm, it is possible to fine adjust the images on the screen with the pixel resolution of 0.012 mm. To make this software calibration possible, each screen possesses two offsets to compensate for misalignment in both the x and y directions. To position the screens and auxiliary lenses, a parameter for location is available.

By modifying the deflection angle of the mirrors, the image displays may be mounted at angles other than the perpendicular plane described herein. The primary limitation to how closely they are mounted together (near parallel tracks) depends on the size of the mirrors. Obviously, those of skill in the art would also work out the additional modifications to, for instance, the belt systems, if the image displays are not perpendicular to the line of sight.

The virtual image has no direct correspondence in the mechanics, rather it consists of the real image with the screens and the auxiliary lens both having a mechanical correspondence.

The beam deflection unit holds the mirrors which are used to set the vergence of the optical system and is movable. Dependent of the position, the mirror turns to the appropriate angle. Please note that the moving and the rotating motion are not possible independently. This view of the mechanics is visible on the software side as well.

Three stepper motors are used to accomplish the movements of the auxiliary lenses, the displays and the mirrors. Each motor serves a belt running through two wheels. The belt forms a closed loop. The optical parts are connected to the belts. Both displays are connected to the same belt. Therefore, when the belt is in action, both displays move symmetrically, i.e. towards each other or the inverse. The same system of fixation accounts to the auxiliary lens and to the mirrors so to make them perform a symmetrical motion.

Figure 8:
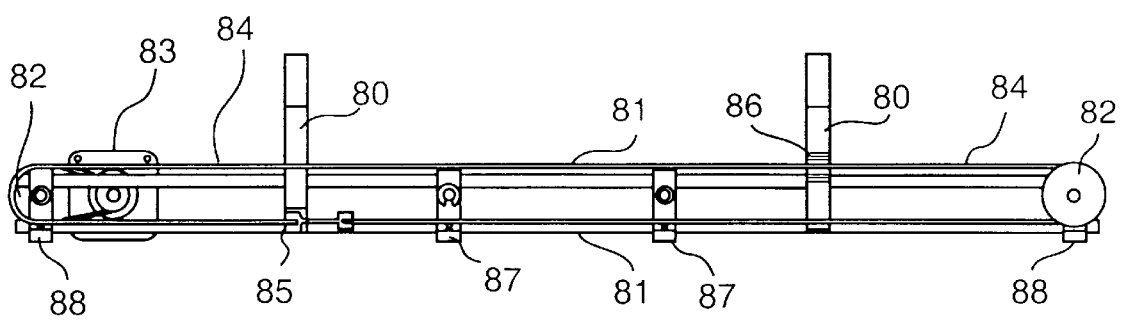
FIG. 8 is a front elevation view of the auxiliary lens component and related features of a vision screener in accordance with a preferred embodiment of the present invention.

FIG. 8 sets forth an illustration of how the stepper motor works in connection with, for instance, the auxiliary lenses 80. The auxiliary lenses 80 are moveably mounted to the support bars 84. A continuous loop belt 81 is driven by cogwheels 82. Those cogwheels 82 are, in turn, moved by the stepper motor 83. The top of the belt 81 is connected to one of the lenses 80 at fixture point 86. The bottom of the belt 81 is connected to the other lens 80 at fixture point 85. The support bars 84 are in turn carried by the mounts 87 and 88. The inside mounts 87 prevent the lenses 80 from moving too close to each other. The outside frame mounts 88 establish the outside boundary limits of movement of the lenses 80.

All of the positioning of the image display, auxiliary lens and mirror is done using stepper motors with a half step resolution of 800 steps per turn. Using a 2.5 mm driving belt and a 15 cogs cogwheel a step distance s=0.0469 mm can be achieved.

For the mirror adjustment unit, this belt is directly used to position the mirror sliders as shown and described earlier in connection with FIG. 6. The rotation of the mirrors is slightly more difficult as the angle can be seen as a function of the position. The mechanism used is shown in FIG. 7, easily allows for tilt adjustments as well.

The positioning system for the auxiliary lenses and the screens both use a driving cogwheel with 15 cogs which drives a second shaft holding a 30 cogs cogwheel. The driving belt for the sliders then lies on a second 30 cogs-cogwheel on the same shaft effectively resulting in the same step resolution as the mirror positioning system.

Specific Discussion of an Embodiment of the Vision Screener

Figure 9:
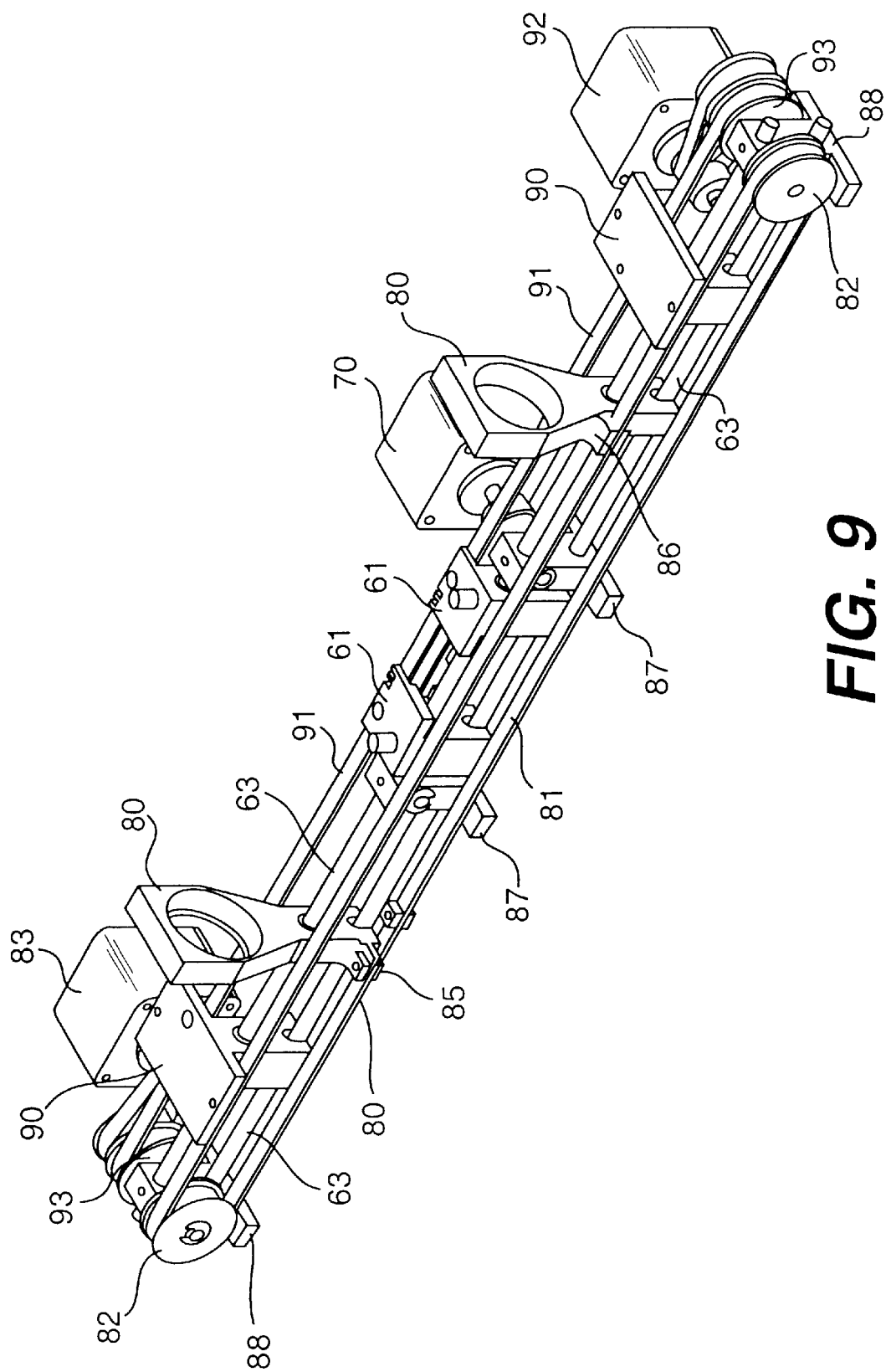
FIG. 9 is a perspective view of a portion of the operative components of a vision screener in accordance with a preferred embodiment of the present invention.
Figure 10:
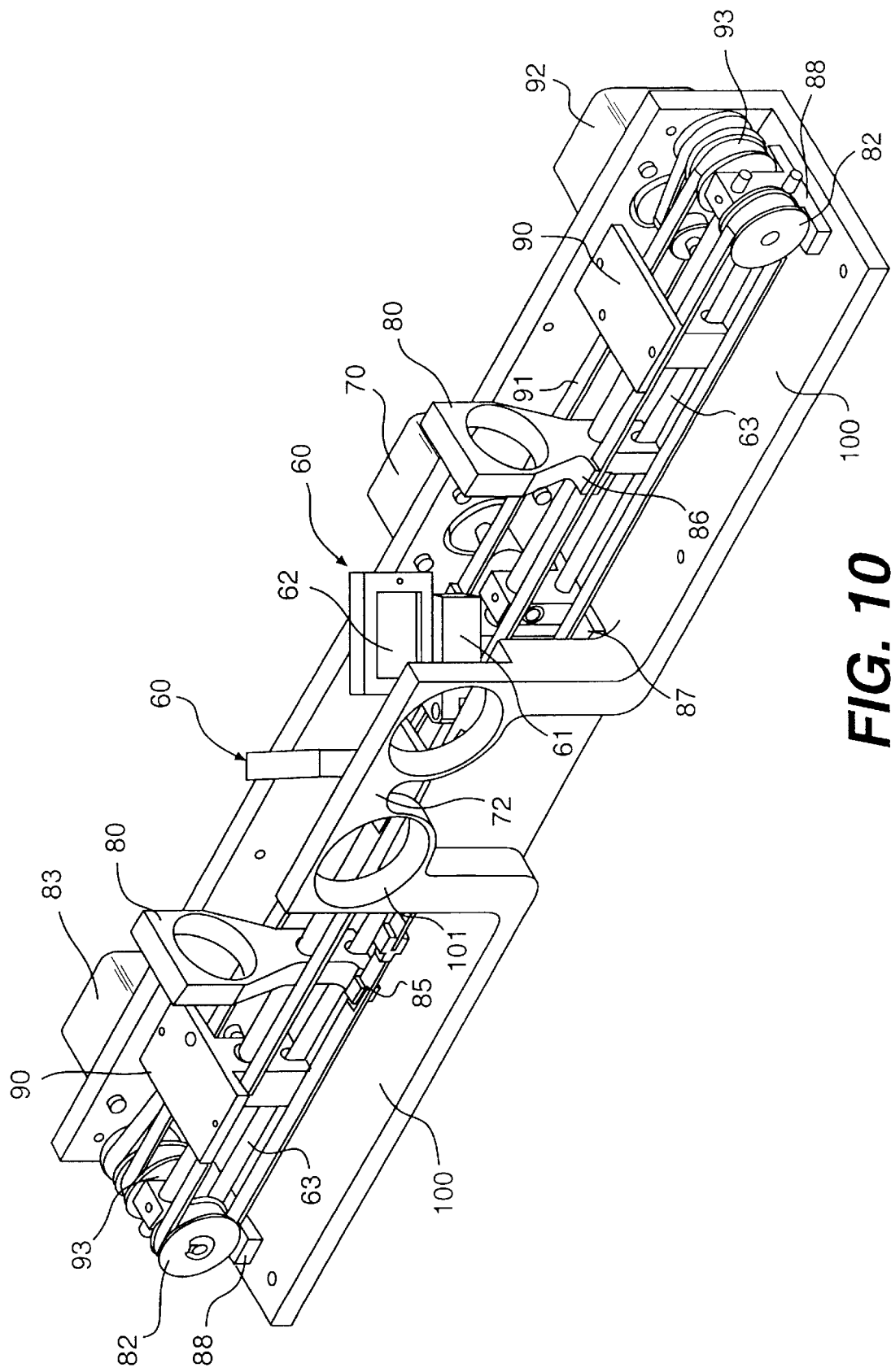
FIG. 10 is a perspective view of the inside components of a vision screener in accordance with a preferred embodiment of the present invention.

Turning now to FIGS. 9 and 10, the inside of a vision screener with virtually all of its mechanical components is illustrated. These components would fit inside the casing 25 illustrated in FIG. 2. The light occluding casing 25 can serve itself as the platform for the mechanics contained inside. Alternatively, as shown in the drawings, the inside parts can be mounted onto a platform 100 that is then itself connected to the inside of the casing 25. Each of the major components of the vision screener 20 is illustrated in FIGS. 9 ad 10.

First, an image display platform 90 is shown mounted onto support bars 63. The image display itself is not shown.

It is fixed onto the surface of the platform 90. The image display platforms 90 are connected to belt 91 that is in turn rotated by cogwheels 93. Those cogwheels 93 are in turn rotated by the image display motor 92. The operation of the image displays 90 in connection with the belt 91 is the same as previously explained in connection with the auxiliary lenses 80. The only difference is that they are rotated by a separate belt 91 and actuated by a separate motor 92. In this way, the image display screen position can be independently manipulated. The auxiliary lenses 80 are as described in connection with FIG. 8. They are mounted along the same support bars 63 so that the image display screen and the auxiliary lens 80 will be in alignment. Similarly, the mirror assemblies 60 are mounted onto the support bars 63 and are positioned through use of the mirror positioning motor 70 and as described in more detail in connection with FIGS. 6 and 7.

Referring specifically now to FIG. 10, the assembly includes a viewer 72 that further includes apertures 101 for front lenses. The viewer is in a fixed position in relation to the vision screener. The support bars 63 are perpendicular to the line of sight between front lenses and the mirrors.

Getting Zero Position

Every motor driven positioning system somehow needs to know where it is located. Using stepper motors makes it possible to count the steps and multiply them with a known step width of 0.0469 mm as in the preferred system described above. In order to make the counting of steps useful, a calibration point at which the physical position is known must be found where the step counter can be set at 0. In the preferred embodiment this is done using infrared, reflexive optocouplers which act as end switches at the same time. Optocouplers are mounted on the baseplate and look upward. They are active as long as a lens or an image display platform or mirror assembly is positioned just above them. They are used to find a calibrated position from which the steps then can be counted.

The end switch emits a infrared light beam, which is reflected by each moving component as soon as it reaches a designated end position. The reflected light is then detected by the sensor and sent to the controlling computer which then knows that the slider has reached its end position.

Calibration of the Optics

The vision tester must also be calibrated so that the image on the different displays are properly visible and in alignment. There are multiple methods for calibrating these types of instruments that are known to those of skill in the art. One method includes the use of parallel slits to center the image and properly tilt the mirror. Another common methodology includes the use of light beams and photodiodes to properly center displayed images. The entire calibration process is repeated for each of the right and left portions of the vision screener (right and left eyes).

Vision Screener System

In a preferred embodiment, the vision screener acts as part of an overall vision testing system. This system allows for self-testing, customized testing, recordation and compilation of test results. The preferred system includes an administrating computer, one or more vision screeners, and system software. The software is loaded onto either an isolated PC or one PC on a local network.

The software, via the administrating computer, enables an administrator to interface with and configure the vision screener's test sequence. It allows the administrator to enter a patient's identifying information and select the job standard to which the results will be compared. Additionally, custom testing may be input by the administrator. Once configured, the software alone will enable the vision screener to begin a patient's screening.

The vision screener takes the configuration data and guides the patient through selected vision tests via verbal instructions and visual examples. Each test is preceded by verbal instructions prerecorded and played to the patient via integral speakers or an optional set of headphones. Test patterns are presented individually to the patient. The patient indicates his/her response to each pattern via a joystick. Each response is recorded and another image displayed until the test sequence is completed. The number of images presented to the patient varies depending on the number and sequence of correct and incorrect responses. This customized response to a patient's input allows for much more precise and accurate testing. The different tests that can be performed by the vision screener include visual acuity, contrast sensitivity, color vision, binocularity, near heterophoria, stereo test, and any other tests that are common in the industry or that may be developed. The advanced techniques with respect to interacting with the patient based on the patient's individual responses also reduces variations in the results caused by administrator error or too few tests being presented.

A preferable testing technique used, for instance, in connection with color vision testing, is a bracketing technique specifically referred to as the MOBS technique. This specific testing methodology is designed to automate the subjective measurement of vision limits. Tyrrell, R. and Owens, D., *A Rapid Technique To Assess The Resting States Of The Eyes And Other Threshold Phenomena: The Modified Binary Search* (*MOBS*), Behavior Research Methods, Instruments & Computers, 1988, 137–141. The MOBS technique provides for efficient, precise, and most importantly, accurate results. By programming the MOBS technique into the vision screener software, the subjective decisions of a human administrator are bypassed. Natural human error and/or human bias are removed from the test.

Stimuli to be presented for vision testing vary within a given range defined by limits such as "non visible" and "easily visible". MOBS starts by presenting a stimulus in the middle of the range (e.g. color is "half the way" between green and red, size is between small and big). Subjects report whether the stimulus was "visible" or "not visible". Features of the next stimulus presented are adjusted depending on subjects answer. The amount of changes in feature of stimulus become increasingly smaller after every answer. Sometimes, after a reverse in direction of change is required (e.g. due to reverse of answer or in order to test validity of answer), the amount of change may become larger again. The procedure typically stops after a given amount of "reversing" have taken place.

Brief Description of MOBS (A) Test starts presenting target with feature at halfway between boundaries of test range.

(B) Depending on subjects answer (correct or false), intensity of feature (color, contrast or whatever is tested) is increased or decreased by half the amount of difference of intesity given by values of boundaries.

(C) After two consecutive answers with the same sign (correct or false) have been recorded, feature of target is set to value corresponding to opposite of range of actual testing (i.e. outside actual test range), to test for consistence of answer (will he or she really give an opposite answer?). If test result OK, boundaries are changed to reduce test range and test proceeds with B).

(D) Test stops when stopping criterion will be fulfilled.

The vision screener is comprised of three subsystems—imaging, projection, and controlling systems. The imaging system is used to display the test images on the image displays. The projection system processes the images. The control systems drives the image and projection systems while providing the interface to the administrating computer and the patient. The control system also supports the circuits for the speakers, joystick, image displays, and the projection system motors.

As different tests are developed, or as different test distances become relevant for a particular tester, new software can be developed and programmed into the vision screener. Using the formulas noted in this description, the vision screener can be manipulated and the components moved around to create new and variable tests. For instance, numerous different shaped and sized images may be displayed. The auxiliary lens and the image display may be moved about together or independently to create different virtual images. Even the mirrors can be moved to account for the vergence in different tests. All of this variability is controlled by different software and computers at the control of the tester or administrator.

Also, different security features may be incorporated into the system. These features may include hardware or software safeguards or both.

That which has been described above is a compact, customizable vision testing device capable of producing and storing fast and accurate test results to a wide variety of test subjects, and with a wide variety of test functions. While the invention has been described in connection with what is presently considered to be the most practice and preferred embodiments, it is to be understood that the invention is not limited to the disclosed embodiment, but, on the contrary, is intended to cover various modifications and equivalent arrangements included within the spirit and scope of the appended claims, which scope is to be accorded the broadest interpretation so as to encompass all such modifications and equivalent structures.

What is claimed is:

1. A vision test apparatus comprising:
   a light-occluding casing;
   a viewer connected to the casing and comprising a front lens;
   a mirror rotatably mounted to the inside of the casing and behind the front lens;
   an image display movably mounted to the inside of the casing; and
   an auxiliary lens movably mounted to the inside of the casing and in alignment between the image display and the mirror;
   whereby an image that is displayed on the image display passes through the auxiliary lens, reflects off of the mirror and passes through the front lens.

2. A vision test apparatus according to claim 1, further comprising a support bar that is fixedly mounted to the inside of the casing and further wherein the image display and the auxiliary lens are movably mounted onto the support bar.

3. A vision test apparatus according to claim 1, wherein the image display and auxiliary lens are fixedly connected to each other.

4. A vision test apparatus according to claim 1, further comprising a second front lens, a second mirror, a second auxiliary lens and a second image display.

5. A vision test apparatus according to claim 1, wherein the image display is an LCD screen.

6. A vision test apparatus according to claim 1, wherein the apparatus creates a virtual visual distance from the viewer to the image of from 14 inches to 20 feet.

7. A vision test apparatus according to claim 1, further comprising a computer for controlling the image presented on the display and movement of the mirror, display and auxiliary lens.

8. A vision test apparatus according to claim 1, further comprising separate motors for actuating movement of the mirror, display and auxiliary lens.

9. A vision test apparatus comprising:
   a light-occluding casing;
   a viewer connected to the casing and comprising right and left front lenses;
   a right mirror and a left mirror, each mirror rotatably mounted to the inside of the casing, the right mirror behind the right front lens and the left mirror behind the left front lens,
   a right image display and a left image display movably mounted to the inside of the casing wherein the image displays face each other with each display being generally perpendicular to a line between the corresponding front lenses and mirrors.

10. A vision test apparatus according to claim 9, further comprising right and left auxiliary lenses movably mounted to the inside of the casing and in alignment between the right and left image displays and corresponding right and left mirrors.

11. A vision test apparatus according to claim 10, further comprising a computer for controlling the image presented on the display and movement of the mirror, display and auxiliary lens.

12. A vision test apparatus according to claim 10, further comprising separate motors for actuating movement of the mirror, display and auxiliary lens.

13. A vision test apparatus according to claim 9, wherein the image displays are LCD screens.

14. A vision test apparatus according to claim 9, wherein the apparatus creates a virtual visual distance from the viewer to the image of from 14 inches to 20 feet.

15. A vision test apparatus comprising:
   a light-occluding casing:
   viewing means fixedly attached to the casing;
   mirror means rotatably mounted behind the viewing means for reflecting images from an image display means to the viewing means;
   image display means for generating images; and
   an auxiliary lens movably mounted to the casing between the image display means and the mirror means,
   whereby an image generated by the image display means passes through the auxiliary lens, is reflected off of the mirror means, and passes through the viewing means.

16. A vision test apparatus according to claim 15, wherein the viewing means further comprises a front lens.

17. A vision test apparatus according to claim 15, wherein the apparatus creates a virtual visual distance from the viewer to the image of from 14 inches to 20 feet.

18. A vision test apparatus according to claim 15, further comprising a computer means for controlling the images presented on the image display means and the movement of the mirror means, image display means and auxiliary lens.

19. A vision test apparatus according to claim 15, further comprising separate actuator means for moving the mirror means, image display means, and auxiliary lens.

* * * * *